United States Patent
Wu

(10) Patent No.: US 10,660,620 B2
(45) Date of Patent: May 26, 2020

(54) SPERM COLLECTION DEVICE

(71) Applicant: LOVER HEALTH SCIENCE AND TECHNOLOGY CO., LTD., Huzhou (CN)

(72) Inventor: Wei Wu, Huzhou (CN)

(73) Assignee: LOVER HEALTH SCIENCE AND TECHNOLOGY CO., LTD., Huzhou (CN)

( * ) Notice: Subject to any disclaimer, the term of this patent is extended or adjusted under 35 U.S.C. 154(b) by 333 days.

(21) Appl. No.: 15/607,891

(22) Filed: May 30, 2017

(65) Prior Publication Data

US 2017/0258456 A1 Sep. 14, 2017

Related U.S. Application Data

(63) Continuation of application No. PCT/CN2014/093805, filed on Dec. 15, 2014.

(30) Foreign Application Priority Data

Nov. 28, 2014 (CN) .......................... 2014 1 0700161

(51) Int. Cl.
| | |
|---|---|
| *A61F 5/44* | (2006.01) |
| *A61B 10/00* | (2006.01) |
| *A61H 19/00* | (2006.01) |
| *A61H 15/00* | (2006.01) |

(Continued)

(52) U.S. Cl.
CPC ............ *A61B 10/0058* (2013.01); *A61F 5/44* (2013.01); *A61H 7/007* (2013.01); *A61H 15/0078* (2013.01); *A61H 19/00* (2013.01); *A61H 19/30* (2013.01); *A61H 19/32* (2013.01); *A61H 23/02* (2013.01); *A61B 10/00* (2013.01); *A61H 2015/0014* (2013.01); *A61H 2201/1654* (2013.01); *A61H 2201/1671* (2013.01);

(Continued)

(58) Field of Classification Search
CPC ....... A61B 10/0058; A61F 5/44; A61H 7/007; A61H 15/0078; A61H 19/00
USPC ........................................................ 604/349
See application file for complete search history.

(56) References Cited

U.S. PATENT DOCUMENTS 5,466,235 A * 11/1995 Shubin, Sr. ............ A61H 19/00
600/38
5,782,818 A * 7/1998 Shubin ............... A61B 10/0058
600/38

(Continued)

FOREIGN PATENT DOCUMENTS

| CN | 1366867 A | 9/2002 |
|---|---|---|
| CN | 101247763 A | 8/2008 |

(Continued)

OTHER PUBLICATIONS

The World Intellectual Property Organization (WIPO) International Search Report and Written Opinion for PCT/CN2014/093805 dated Jul. 10, 2015 8 Pages.

*Primary Examiner* — Andrew J Mensh
(74) *Attorney, Agent, or Firm* — Anova Law Group, PLLC

(57) ABSTRACT

The present disclosure provides a sperm collection device, including at least one driving unit, and a soft main body wrapping the at least one driving unit. The soft main body includes a penis passage. The at least one driving unit is configured to vibrate an inner wall of the penis passage and provide a squeezing force to the penis passage.

11 Claims, 7 Drawing Sheets

(51) Int. Cl.
*A61H 7/00* (2006.01)
*A61H 23/02* (2006.01)
(52) U.S. Cl.
CPC .. *A61H 2201/50* (2013.01); *A61H 2201/5097* (2013.01); *A61H 2205/087* (2013.01)

(56) References Cited

U.S. PATENT DOCUMENTS

| | | | | |
|---|---|---|---|---|
| 6,338,721 | B1* | 1/2002 | Lebecque | A61F 5/41 600/38 |
| 8,663,087 | B2* | 3/2014 | Kolar | A61H 9/0021 600/38 |
| 8,900,120 | B2* | 12/2014 | Lewis | A61H 19/00 600/38 |
| 2014/0135650 | A1* | 5/2014 | Wu | A61B 10/0058 600/573 |

FOREIGN PATENT DOCUMENTS

| | | |
|---|---|---|
| CN | 202005872 U | 10/2011 |
| CN | 102657542 A | 9/2012 |
| CN | 202751411 U | 2/2013 |
| CN | 204306846 U | 5/2015 |

\* cited by examiner

SPERM COLLECTION DEVICE

CROSS-REFERENCES TO RELATED APPLICATIONS

This application is a continuation application of PCT Patent Application No. PCT/CN2014/093805, filed on Dec. 15, 2014, which claims priority to Chinese Patent Application No. 201411070016.1, entitled "SPERM COLLECTION DEVICE" filed on Nov. 28, 2014, the entire contents of both of which are incorporated herein by reference.

FIELD OF THE DISCLOSURE

The present disclosure relates to the field of medical device technologies and, more particularly, relates to a device for collecting sperm.

BACKGROUND

Andrology is getting more attention in domestic and foreign medicine. Semen collection is required in clinical prenatal and postnatal care, family planning, infertility, and male reproductive system of many diseases need to take. Clinically, a widely-used semen collection method is masturbation by a patient. Due to objective situations, it is difficult for a patient to provide semen at the hospital using this method, or semen collection at the hospital using this method need to overcome a variety of psychological barriers and take a lot of time. This type of semen collection method neither provides fast, convenient, or sterile collection process, nor facilitates tests and analysis, and may even cause errors.

Currently, sperm collection devices available on the market have a simple structure, the main body of which has a certain hardness, and is not comfortable to use. Further, most existing sperm collection devices require a user to manually squeeze the device for providing stimulation to the penis. Poor stimulation effect, difficult to achieve excitement, long collection time, and many other shortcomings exist for existing sperm collection devices.

The disclosed method and system are directed to solve one or more problems set forth above and other problems.

One aspect of the present disclosure provides a sperm collection device, including at least one driving unit, and a soil main body wrapping the at least one driving unit. The soft main body includes a penis passage. The at least one driving unit is configured to vibrate an inner wall of the penis passage and provide a squeezing force to the penis passage.

Other aspects of the present disclosure can be understood by those skilled in the art in light of the description, the claims, and the drawings of the present disclosure.

BRIEF DESCRIPTION OF THE DRAWINGS

The following drawings are merely examples for illustrative purposes according to various disclosed embodiments and are not intended to limit the scope of the present disclosure.

DETAILED DESCRIPTION

Reference will now be made in detail to exemplary embodiments of the invention, which are illustrated in the accompanying drawings. Hereinafter, embodiments consistent with the disclosure will be described with reference to the drawings. Wherever possible, the same reference numbers will be used throughout the drawings to refer to the same or like parts. It is apparent that the described embodiments are some but not all of the embodiments of the present invention. Based on the disclosed embodiments, persons of ordinary skill in the art may derive other embodiments consistent with the present disclosure, all of which are within the scope of the present invention.

Figure 1:
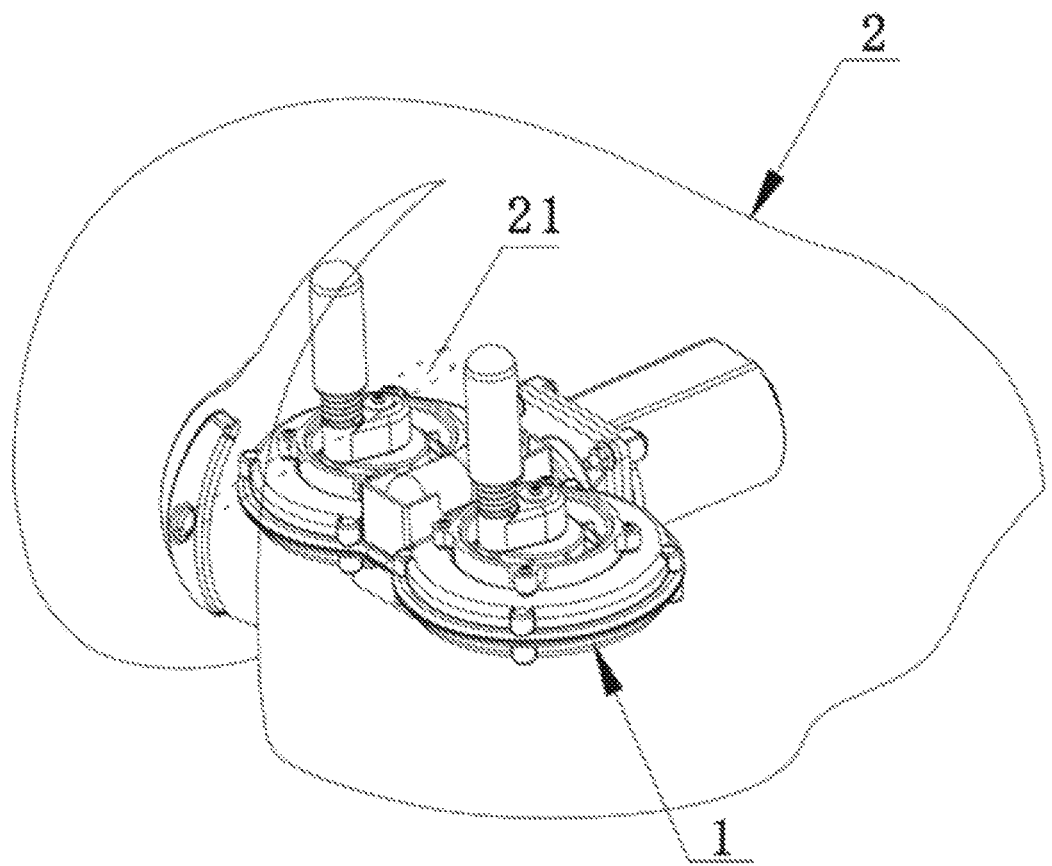
FIG. 1 is a structural diagram illustrating an exemplary sperm collection device consistent with the disclosed embodiments.

As shown in FIG. 1, the present disclosure provides a sperm collection device, including: at least one driving unit 1 and a soft main body 2. The disclosed sperm collection device may also be referred as sexual stimulation device. The soft stain body 2 may wrap the at least one driving unit 1. The soft main body 2 includes a penis passage 21. In an exemplary embodiment, the soft main body 2 not only wraps outer edges of the at least on driving unit 1, but also wraps all components of the at least one driving unit 1 entirely.

Figure 2:
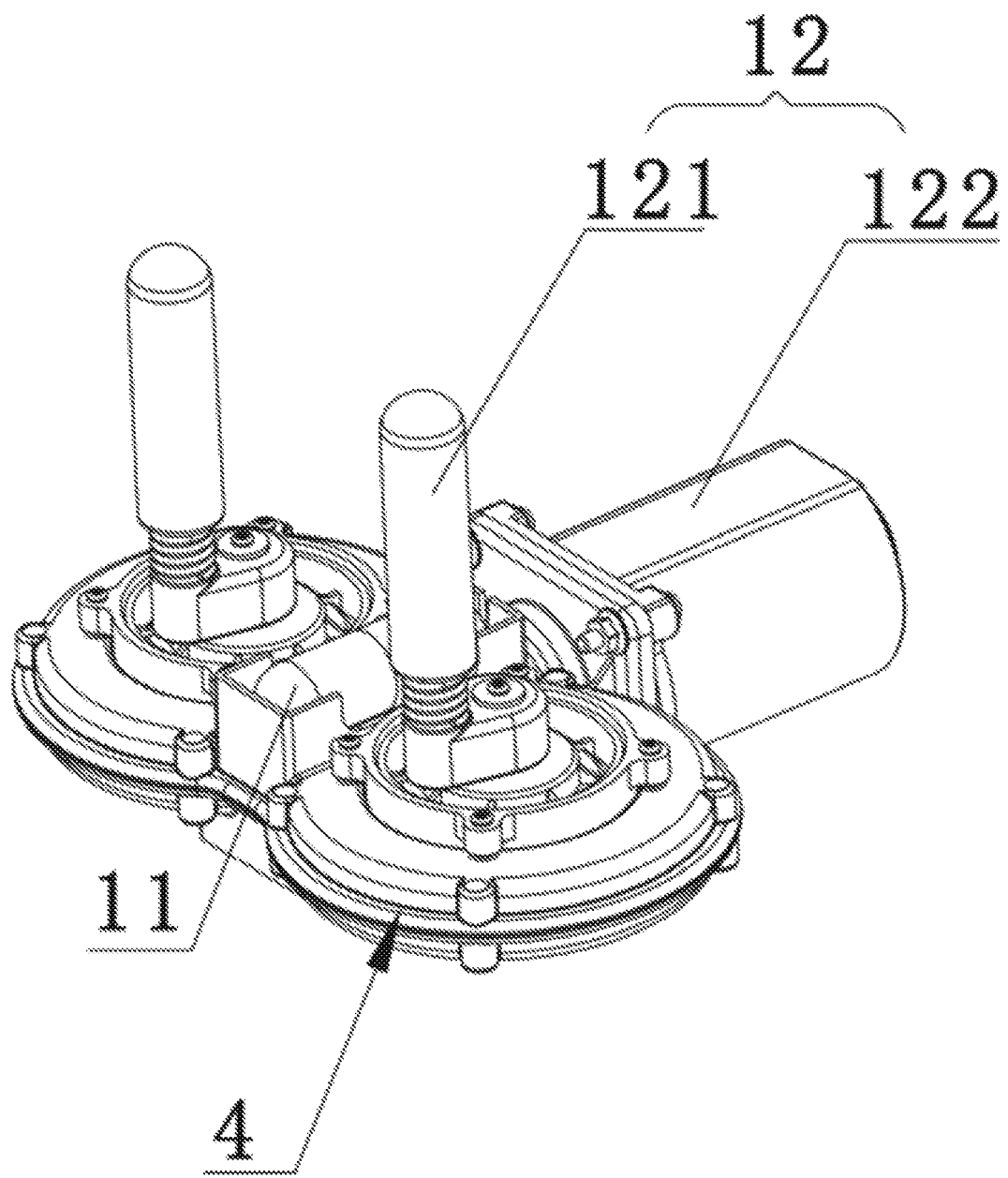
FIG. 2 is a structural diagram illustrating a driving unit of an exemplary sperm collection device consistent with the disclosed embodiments.

In on embodiment, as shown in FIG. 2, the sperm collection device may include two driving units 1 which are, respectively, a first drive assembly 11 for generating vibrations on an inner wall of the penis passage 21, and a second drive assembly 12 for providing squeezing and contraction forces onto the penis passage 21. In other embodiments, the sperm collection device may include only the first drive assembly 11 or the second drive assembly 12.

The first drive assembly includes a first motor, the first motor being a vibration motor. The second drive assembly 12 may include one or more moving rods 121 and second motor 122 which drives the one or more moving rods 121 to move along a specific/preset trajectory. The specific trajectory, as used herein, may refer to a curve, a straight line, or a combination of a curve and a straight line. The movement may include moving in space and/or rotation. The second drive assembly 12 may further include a guiding structure for guiding moving rod 121 to move along the specified trajectory when the moving rod 121 is driven the second motor 122. In some embodiments, the guiding structure may support trajectory switching. For example, two trajectories (e.g., a straight line and a curve) may be configured to a moving rod 121. The beginning and ending point of the trajectories may be the same. Based on user selection, the moving rod 121 may be switched between the two trajectories for different intensity stimulation.

In some embodiments, two moving rods 121 may be configured to perform repeated movements along an arcuate curve (i.e. moving back and forth along the curve) when being driven by rotations of the second motor 122, and the directions of movements of the two moving rods 121 are opposite. For example, a first moving rod is driven to move along a first semi-elliptical trajectory in a clockwise direction, while the second moving rod is driven to move along a second semi-elliptical trajectory in a counter-clockwise direction. The first semi-elliptical trajectory and the second semi-elliptical trajectory may be symmetrical, the axis of symmetry being the penis passage 21. Further, a distance from the first moving rod to the axis and a distance from the second moving rod to the axis may be the same during movement. That is, the two moving rods 121 may move in substantially parallel when being driven by the second motor 122.

In one embodiment, the second drive assembly 12 may include two moving rods 121 disposed on both sides of the penis passage 21. In another embodiment, the second drive assembly 12 may include one moving rods 121 or more than two moving rods 121.

Under the driven force of the second motor 122, a moving rod 122 may perform movements that exert pressure on the penis passage 21. The movements may include repeated linear movement, repeated curve movement, and/or rotation. The rotation of a moving rod 122 may be 360-degree rotation. The movements may cause the penis passage 21 to be squeezed or contracted. In some embodiments, the second drive assembly 12 may include two motors, one for driving the rotation of the moving rods, and the other for driving the moving rods to move along preset trajectories.

Figure 5:
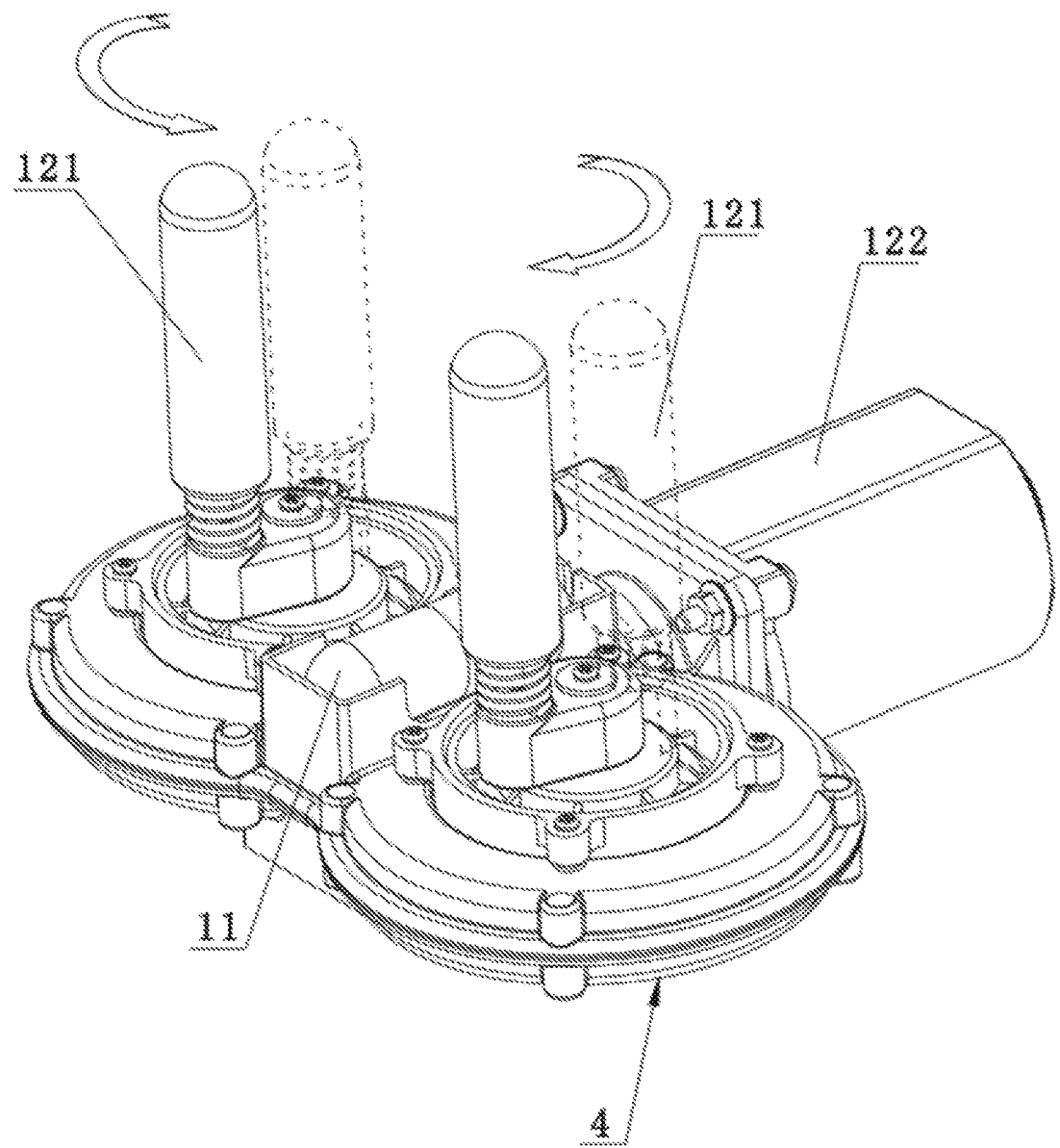
FIG. 5 is a schematic view illustrating the motion of a moving rod consistent with the disclosed embodiments.

As shown in FIG. 5, the solid lines and the dotted lines corresponding to two moving rods 121 illustrate a schematic view of the two moving rods 121 in a moving state. When moving under the force of the second motor 122, the two moving rods 121 may gradually approach each other until a minimum distance is reached, and then gradually separate from each other until a maximum distance is reached. The two moving rods 121 may repeat such cycle of gradually approaching and separating. When gradually approaching each other, the two moving rods 121 may simultaneously produce a pressing force on both side walls of the penis passage 21, and the penis passage 21 contracts accordingly to produce a covering/wrapping three on the penis. Further, as the distance between the two moving rods 121 is gradually decreasing, the penis passage 21 is being squeezed by more force, the corresponding wrapping on the penis become tighter, thus enhancing the stimulation effect on the penis.

The second motor 122 may drive both the moving rods 121 integrally. The moving rods 121 may contact the penis passage 21 from top to bottom. When the contacting area is larger, the area for penis stimulation is correspondingly larger, thereby creating better stimulating effect. Further, during movement of the moving rods 121, as the contact area gets greater, the pressing force of the moving rods 121 to the penis passage 21 become more even.

In some embodiments, the two moving rods 121 may be symmetrically disposed on opposite sides of the penis passage 21, with the penis passage 21 being the axis of symmetry. The uniformity of squeezing force generated by the two moving rods 121 onto the side walls of the penis passage 21 may be enhanced. However, locations of the moving rods in the present disclosure is not limited thereto.

Further, while the moving rods 121 is moving back and forth in a preset path for allowing the penis passage 21 to be repeatedly contracted and released, the first drive assembly 11 may vibrate the inner wall of the penis passage 21, which further enhances stimulation effect on the penis and greatly enhances the user's excitement. Accordingly, the time taken for sperm collection can be greatly reduced.

In some embodiments, the moving rods 121 may each have a cylindrical shape. With curved outer surface of the moving rods 121, during movements, the two moving rods 121 may produce uniform pressing force to the penis passage 21. However, the present disclosure does not limit the shape of the moving rods 121. In other embodiments, the shape of the moving rods 121 may be spherical.

In some embodiments, moving rod sleeves 123 made of flexible material may be provided for the moving rods 121. Accordingly, softness of the moving rods 121 can be enhanced. In one embodiment, the moving rod sleeve 123 is made of silica gel. However, the present disclosure is not limited thereto.

Figure 4:
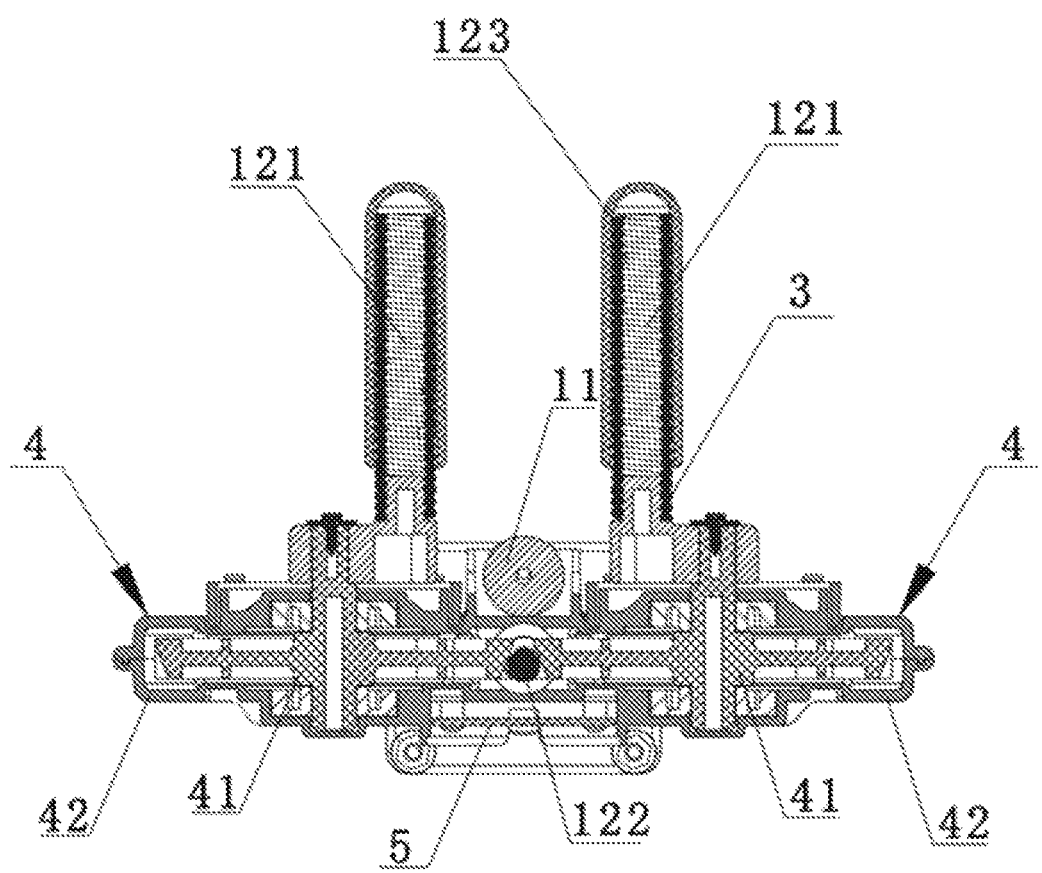
FIG. 4 is a schematic cross-sectional view oldie driving unit in FIG. 2 consistent with the disclosed embodiments.

In some embodiments, the disclosed sperm collection device may further include cushion members 3 disposed against the moving rods 121, respectively. In one embodiment, as shown in FIG. 4, a cushioning member 3 may include a spring which is wound around an outer surface of a moving rod 121 and is positioned within the moving rod sleeve 123. In another embodiment, the cushion member 3 may be a resilient member made of other resilient material. Further, the quantity of the cushion members 3 may be set in accordance with the number of moving rods 121. When a moving rod 121 is moving, the corresponding cushion member 3 is compressed. Correspondingly, the cushion member 3 generates a force opposite to the direction of the pressing force generated by the movement of the moving rod 121, thereby providing a cushion/buffer against the squeezing force, improving the comfort of the penis during semen collection, and reducing the collection time.

In some embodiments, the sperm collection device may further include one or more transmission assembly 4. As shown in FIG. 4, a transmission assembly 4 may include a drive gear 41 and a housing 42 disposed outside the drive gear 41. The drive gear 41 may connect the second motor 122 with a moving rod 121 to transmit the output of the second motor 122 to the corresponding moving rod 121 and to cause the moving rod 121 to move. The moving speed transmitted to the moving rod 121 may be adjusted by the drive gear 41. In one embodiment, the second motor 122 may be connected to two transmission assemblies 4. The two transmission assemblies 4 may synchronously change the output speed of the second motor 122. Such configuration allows the two moving rods 121 to rotate/move at the same speed and in opposite directions. The number of the transmission assembly 4 of the present disclosure is not limited. In other embodiments, the number of transmission assemblies 4 may be the same as the number of moving rods 121, and the transmission assemblies 4 may have one-to-one correspondences with the moving rods 121. Alternatively, a plurality of moving rods 121 may be driven by one transmission assembly 4 at the same time.

In some embodiments, the first drive assembly 11 may be configured inside the housing 42. Such configuration reduces the volume of the entire device while achieving a desired vibration effect.

In some embodiments, the soft main body 2 may have a shape resembling a human hip. Such configuration further enhances the excitement of the user during sperm collection, greatly reducing the time. The soft main body may have any other proper shapes, and is not limited herein. The soft main body 2 may be made of flexible materials, such as rubber, silicone gel, etc.

In an exemplary embodiment, the sperm collection device further includes a circuit board 5 disposed inside the soft main body 2. The circuit board 5 may be electrically connected to the first drive assembly 1 and the second drive assembly 12. Accordingly, the circuit board 5 is electrically connected to the first motor and the second motor 122.

Figure 3:
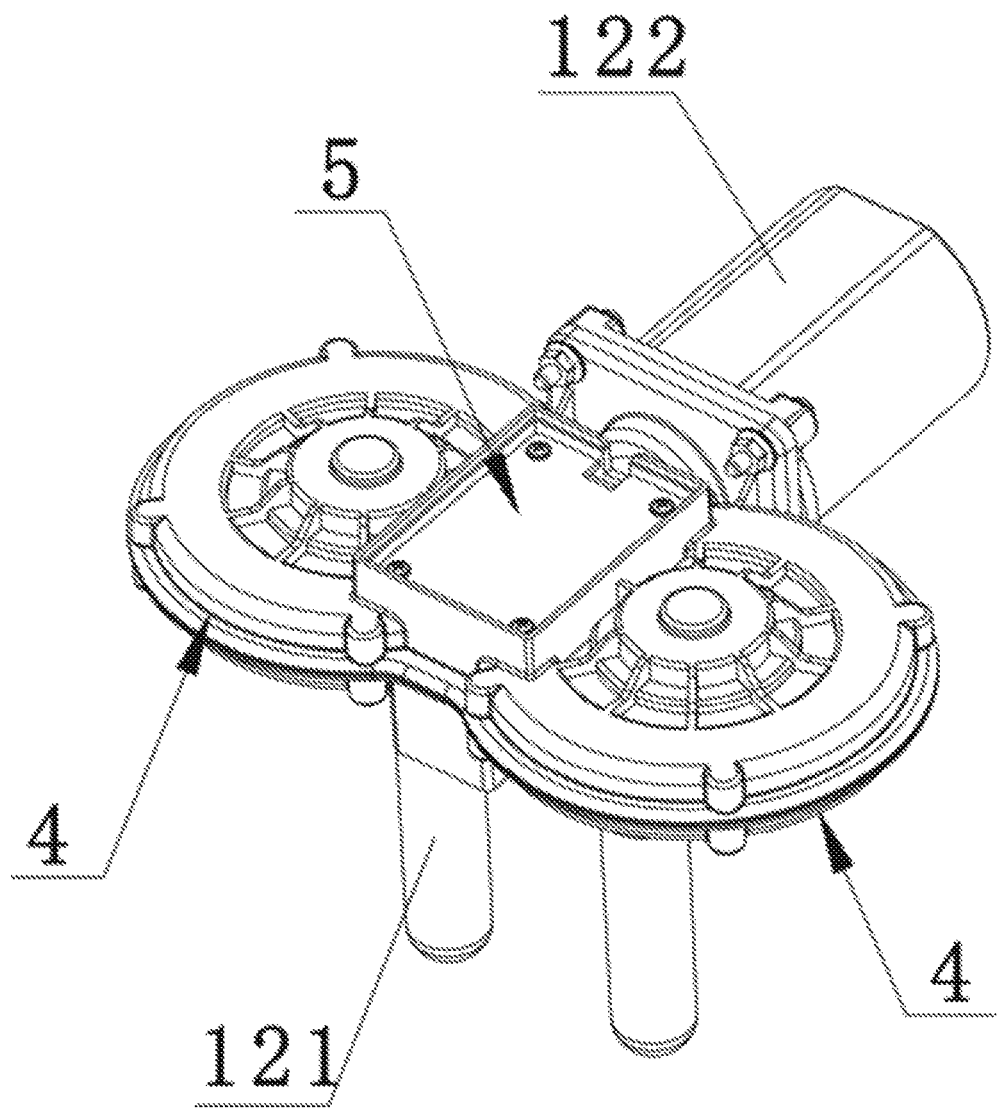
FIG. 3 is a structural diagram illustrating the driving unit in FIG. 2 from another perspective consistent with the disclosed embodiments.

As shown in FIG. 3, the circuit board 5 is disposed at the bottom of the driving unit 1. The first drive assembly 11 and the second drive assembly 12 are controlled by the circuit board 5. The circuit board 5 may include a control module. The control module may be configured to turn on or turn off the first drive assembly 11 and the second drive assembly 12 simultaneously. Further, the circuit board 5 (e.g., the control module) may turn on or off one of the first drive assembly 11 and the second drive assembly 12 based on user's selection. Moreover, the circuit board 5 (e.g., the control module) may adjust the vibration speed of the first drive assembly 11 or movement speed of the second drive assembly 12 based on user input selection. In some embodiments, the first drive assembly 11 and the second drive assembly 12 may be directly connected to an external power supply via a wire. The first drive assembly 11 or the second drive assembly 12 may be turned on or off by connecting or disconnecting the external power supply with the first drive unit 11 and the second drive assembly 12. Further, the vibration speed of the first drive assembly 11 or the movement speed of the second drive assembly 12 can be adjusted by adjusting the input signal of the first drive assembly 11 or the second drive assembly 12 through the circuit board 5.

In an exemplary embodiment, the disclosed sperm collection device may further include one or more control button 6 electrically connected to the circuit board 5. The control button 6 is configured to facilitate user control of the one or more driving unit 1 (e.g., the first drive assembly 11 and the second drive assembly 121 by the circuit board 5. In one embodiment, the user can quickly turn on or off the first drive assembly 11 or the second drive assembly 12 by operating a first control button 6. The vibration speed of the first drive assembly 11 and the movement speed of the second drive assembly 12 can be adjusted by operating a second control button 6. The one or more control buttons may be configured on an outer surface of the soft main body 2.

Figure 6:
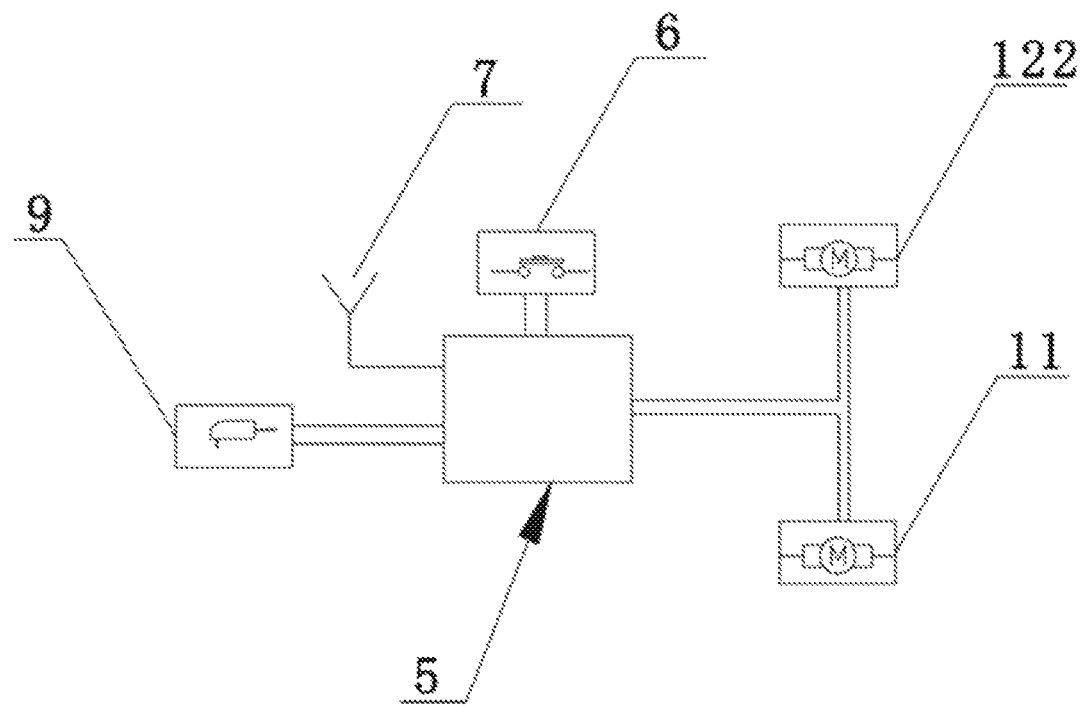
FIG. 6 is a block diagram illustrating a circuit of an exemplary sperm collection device consistent with the disclosed embodiments.
Figure 7:
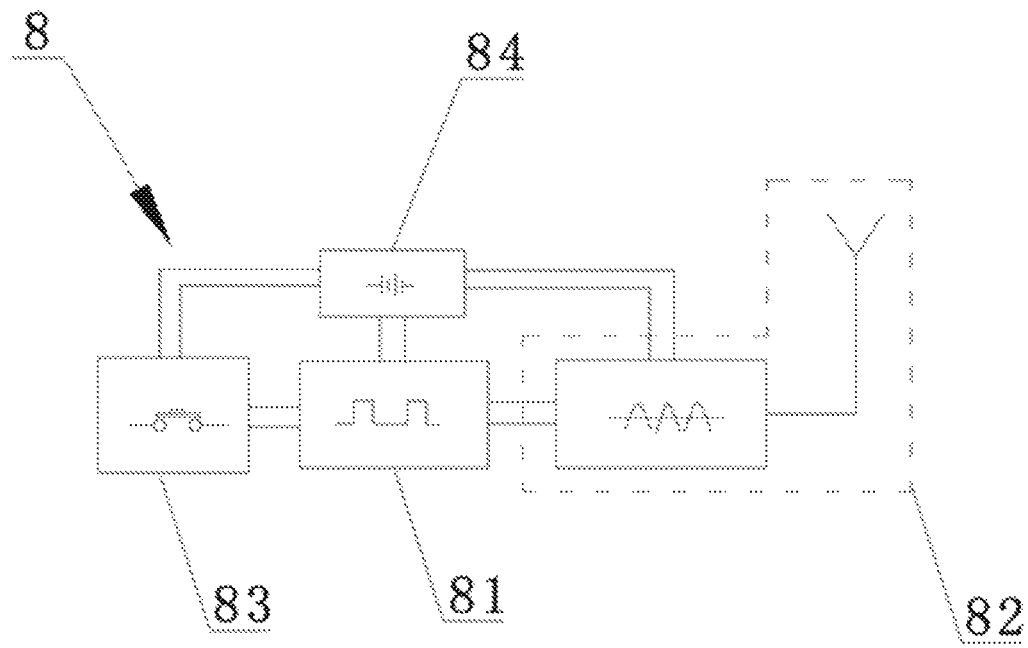
FIG. 7 is a block diagram illustrating a circuit of an exemplary remote control to consistent with the disclosed embodiments.
Figure 8:
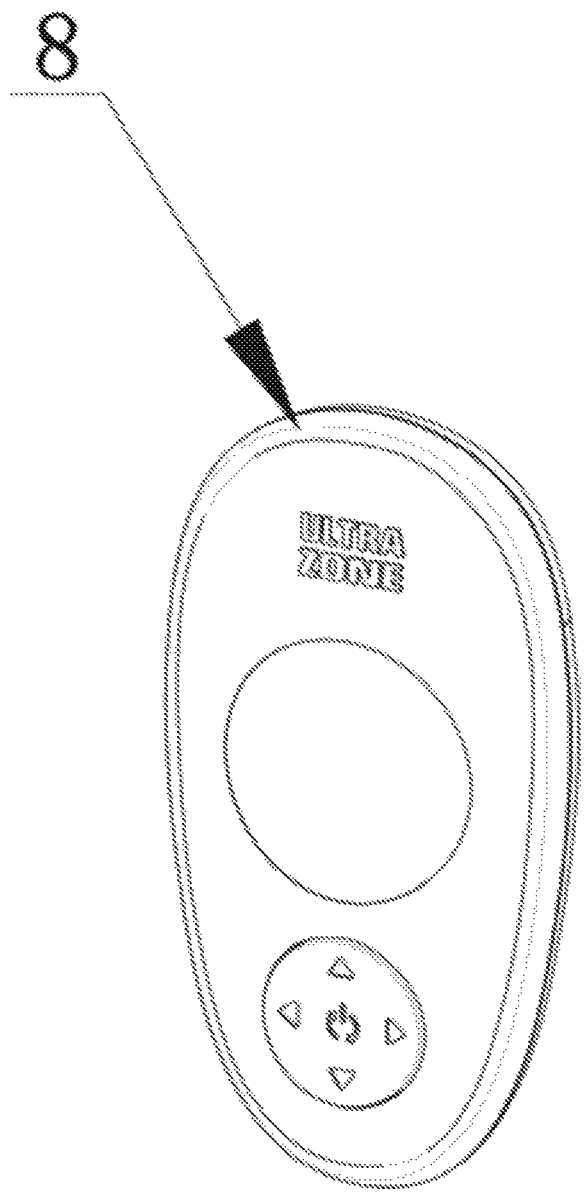
FIG. 8 is a structural diagram illustrating an exemplary remote control consistent with the disclosed embodiments.

In some embodiments, the disclosed sperm collection device may further include a signal receiving module 7 and a remote controller 8. As shown in FIGS. 6-8, the signal receiving module 7 may be configured on the circuit board 5 and electrically connected to components of the circuit board 5 (e.g., the control module). The remote controller 8 includes a remote control circuit board 81, a signal transmission module 82, a remote control key group 83, and a battery 84. When the user presses a key of the remote control key group 83, the signal transmitting module 82 transmits a corresponding wireless signal to the signal receiving module 7. The wireless signal may be a turn-on signal, a turn-off signal, or a gear adjustment signal. In some embodiments, the wireless signal may further indicate which drive assembly the turn-on/off or gear adjustment signal is directed to. That is, the remote controller 8 may control each individual driving unit 1 or all driving unit 1 at the same time. The signal receiving module 7 located within the soft main body 2 receives the wireless signal and passes the signal to the circuit board 5 (e.g., the control module) to control the first drive assembly 11 and/or the second drive assembly 12 accordingly. In one embodiment, the signal transmission module 82 includes a signal transmission circuit and a transmission antenna, and the signal receiving module 7 is a reception antenna.

In some embodiments, the signal receiving module 7 may be a Bluetooth transmission module. The signal transmission module 82 of the remote controller 8 may send control signals to the signal receiving module 7 through Bluetooth communication. In one embodiment, the remote controller 8 may be a smart terminal having Bluetooth communication capabilities. Specifically, the smart terminal may install an application for remotely control the sperm collection device. When being activated, the application may establish communication with the signal receiving module 7 through Bluetooth communication, receive user instructions through a user interface (e.g., the remote control key group 83 may be a touch screen), and send control signals to the signal receiving module 7. That is, a user can conveniently control the driving unit by using the smart terminal, including turning the device on/off, adjusting vibration intensity, adjusting contraction/squeezing intensity, adjusting movement speed, etc. Further, other types of wireless communication technologies, such as infrared, may be used.

In one embodiment, the remote control circuit board 81 is configured to receive user inputs from the remote key group 83, and control the signal transmission module 82 to send a control signal corresponding to the user inputs to the signal receiving module 7 through Bluetooth communication. The signal receiving module 7 is configured to transmit the received control signal to the circuit board 5, and the circuit boards is configured to control the at least one driving unit 1 based on the control signal.

In some embodiments, the sperm collection device may further include a power supply 9. The power supply 9 is electrically connected to the at least one driving unit 1 and the circuit board 5. The power supply 9 is configured to supply power to the circuit board 5, the first drive assembly 11 and the second drive assembly 12. In one embodiment, the power supply 9 is a rechargeable battery provided in the soft main body 2. However, the present invention is not limited thereto. In other embodiments, the power supply 9 may be a charging connector that is connected to the circuit board 5.

In some embodiments, the sperm collection device may further include a sensor for detecting completion of sperm collection. The sensor may be, for example, a weight sensor, a water level sensor, etc. Further, when sperm collection is detected to be completed, the sensor may send a signal to the driving unit to stop vibration and stop driving the moving rods. In some embodiments, the sperm collection device may further include a collection pouch.

In same embodiments, other than being substantially vertical in the soft main body 2, the moving rod 121 may be located substantially horizontally in the soft main body 2. That is, other than generating contraction force at the left and right side of the penis passage 21, the moving rod 121 may generate contraction force at top and bottom side of the penis passage 21. Similarly, the horizontally-placed moving rod 121 may be driven by a motor through a transmission assembly 4, and controlled by the circuit board 5.

In the disclosed sperm collection device, the soft main body 2 include the penis passage 21. During sperm collection, the penis is inserted into the penis passage 21. The at least one driving unit 1 built inside the soft main body 2 may drive the penis passage 21 to vibrate and/or contract. The contraction of the penis passage 21 can produce a great wrapping force to the entire penis, and the vibration of the inner wall of the penis passage can further enhance stimulation effects on the penis, allowing a user to reach excitement stage quickly. Such configuration can greatly reduce collection time and enhance collection efficiency. The penis passage 21 formed inside the soft main body is soft and have a certain degree of flexibility, which provides comfort feelings to the user during usage.

Further, by simultaneously providing the first drive assembly 11 for vibration effects and the second drive assembly 12 for squeezing/contracting effects in the soft main body 2, the stimulation effect can be greatly enhanced and time for sperm collection can be greatly reduced. Further, cushion member 3 is configured on the moving rod 121, which can buffer the force generated during the driven movement of the moving rod 121, improve the comfort of the penis, and further improve the effect of sperm collection. By setting the signal receiving module 7 and the corresponding external remote controller 8 for transmitting the control signal, the user an directly control the working state of the driving unit 1 inside the soft main body 2 through the remote controller 8, which is simple and convenient.

Other embodiments of the disclosure will be apparent to those skilled in the art from consideration of the specification and practice of the invention disclosed herein. It is intended that the specification and examples be considered as exemplary only, with a true scope and spirit of the invention being indicated by the claims.

What is claimed is:

1. A sperm collection device, comprising:
a soft main body including a penis passage,
at least one driving unit configured to vibrate an inner wall of the penis passage and provide a squeezing force to the penis passage, the at least driving unit being wrapped by the soft main body and including a drive assembly, the drive assembly including:
one or more moving rods including two moving rods disposed on opposite side walls of the penis passage, and
a motor configured to drive the one or more moving rods to move back and forth along a curved preset path.

2. The sperm collection device according to claim 1, wherein:
the drive assembly is a first drive assembly, and the motor is a first motor,
the at least one driving unit further includes a second drive assembly, and
the second drive assembly includes a second motor configured to vibrate the inner wall of the penis passage.

3. The sperm collection device according to claim 1, further comprising:
one or more cushion members, each cushion member corresponding to one of the one or more moving rods and being configured to provide a buffer against a force generated by a movement of the corresponding moving rod.

4. The sperm collection device according to claim 1, further comprising:
one or more transmission assemblies configured to connect the motor with the one or more moving rods.

5. The sperm collection device according to claim 4, wherein:
the one or more transmission assemblies are configured to adjust a moving speed of the one or more moving rods.

6. The sperm collection device according to claim 1, wherein the two moving rods are symmetrically located on opposite side walls of the penis passage, an axis of symmetry being the penis passage.

7. The sperm collection device according to claim 1, wherein:
the soft main body has a hip shape.

8. The sperm collection device according to claim 1, further comprising:
a circuit board disposed inside the soft main body,
wherein the circuit board is electrically connected to the at least one driving unit.

9. The sperm collection device according to claim 8, further comprising:
a signal receiving module electrically connected to the circuit board, and
a remote controller including a remote control circuit board, a signal transmission module, a remote control key group, and a battery,
wherein the signal transmission module is configured to send a control signal to the signal receiving module.

10. The sperm collection device according to claim 9, wherein:
the signal transmission module and the signal receiving module support BLUETOOTH® communication,
the remote control circuit board is configured to receive user inputs from the remote key group, and control the signal transmission module to send a control signal corresponding to the user inputs to the receiving module through BLUETOOTH® communication,
the signal receiving module is configured to transmit the received control signal to the circuit board, and
the circuit board is configured to control the at least one driving unit based on the control signal.

11. The sperm collection device according to claim 1, further comprising:
a power supply electrically connected to the at least one driving unit.

* * * * *